United States Patent [19]

Bascomb et al.

[11] Patent Number: 5,565,328
[45] Date of Patent: Oct. 15, 1996

[54] MEASUREMENT OF COLOR REACTIONS BY MONITORING A CHANGE OF FLUORESCENCE

[75] Inventors: Shoshana Bascomb, Davis; Frank J. Swenson, Auburn; Ted Sand, Sacramento, all of Calif.

[73] Assignee: Dade International Inc., Deerfield, Ill.

[21] Appl. No.: 579,089

[22] Filed: Dec. 27, 1995

Related U.S. Application Data

[63] Continuation of Ser. No. 431,194, Apr. 27, 1995, abandoned, which is a continuation of Ser. No. 174,613, Dec. 28, 1993, abandoned, which is a continuation of Ser. No. 16,654, Feb. 9, 1993, abandoned, which is a continuation of Ser. No. 895,149, Jun. 5, 1992, abandoned, which is a continuation of Ser. No. 238,710, Aug. 31, 1988, abandoned.

[51] Int. Cl.$^6$ .......................... C12Q 1/26; H01L 21/306
[52] U.S. Cl. ................................. 435/25; 435/18; 435/29; 435/34; 435/37; 435/968; 436/172
[58] Field of Search ........................... 455/25, 18, 29, 455/34, 37, 968; 436/172

[56] References Cited

U.S. PATENT DOCUMENTS

| | | | |
|---|---|---|---|
| 4,174,384 | 11/1979 | Ullman et al. | 424/8 |
| 4,495,293 | 1/1985 | Shaffar | 436/172 |
| 4,743,561 | 5/1988 | Shaffar | 436/501 |
| 4,912,035 | 3/1990 | Belly et al. | 435/25 |
| 4,954,435 | 9/1990 | Krauth | 435/25 |

FOREIGN PATENT DOCUMENTS

| | | |
|---|---|---|
| 091837 | 2/1983 | European Pat. Off. . |
| 0155330 | 3/1984 | European Pat. Off. . |
| 0278149 | 6/1987 | European Pat. Off. . |
| 8600340 | 1/1986 | WIPO . |

OTHER PUBLICATIONS

Nolte et al., J. Clin. Mirobio., 26:1079–1084 (1988).
Godsey et al., J. Clin. Microbio., 13:483–490 (1981).
8th Edition–Fundamentals of Microbiology Martin Frobisher, ScD., W. B. Saunders Company, pp. 266–268 (1968).
Bascomb, S. *Meth in Microbiol.* 19:105–160, 1987.
Sykes, R. B., and Nordström, K. *Antimicrobial Agents and Chemotherapy* 1(2):94–99, 1972.

Carmel, A., Yaron, A. "An Intramolecularly Quenched Fluorescent Tripeptide as a Fluorogenic Substrate of Angiotensin–I–Converting Enzyme and of Dipeptidyl Carboxypeptidase", Eur. J. Biochem, 87, 265–273 (1978).
Carmel, A., Kellser, E., Yaron, A., "Intramolecularly-Quenched Fluorescent Peptides as Fluorogenic Substrates of Leucine Aminopeptidase and Inhibitors of Clostridial Aminopeptidase", J. Biochem, 73, 617–625 (1977).
Fleminger, G., Carmel, A., Goldenberg, D., Yaron, A., "Fluorogenic Substrates For Bacterial Aminopeptidase P and Its Analogs Detected in Human Serum and Calf L Lung," Eur. J. Biochem, 125, 609–615 (1982).
Ando, T. et al., "Pyruvate as a Fluorescence Quencher: A New Spectroscopic Assay for Pyruvate Reactions", Anal. Biochem. 129, 170–175 (1983).
Bascomb, S., "Enzyme Tests in Bacterial Identification", Methods in Microbiol., vol. 19, ISBN 0–12–521519–3, 105–160 (1987).
Blumberg, W. E., Doleiden, F. H. and Lamola, A. A., Hemoglobin Determined in 15 ul of Whole Blood by "Front Face" Fluorometry, Clin. Chem. 26/3, 409–413 (1980).
Florentin, D., Sassi, A. Roques, B. P., "A Highly Sensitive Fluorometric Assay for Enkephalinase, a Neutral Metalloendopeptidase That Releases Tyrosine–Glycine–Glycine from Enkephalins", Anal. Biochem. 141, 62–69 (1984).
Toro, G., Ackermann, P. G., "Practical Clinical Chemistry", c. 1975 Little Yaron, A., Carmel, A., Katchalski–Katzir, E., "Intramolecularly Quenched Fluorogenic Substrates for Hydrolytic Enzymes,", Anal. Biochem. 95, 228–235 (1979).

*Primary Examiner*—Elizabeth C. Weimar
*Assistant Examiner*—Abdel A. Mohamed
*Attorney, Agent, or Firm*—Cynthia G. Tymeson

[57] ABSTRACT

The present invention relates to a method to determine the concentration of an unknown substance in a colorimetric reaction using a fluorometric reader. The change in color can be monitored by observing the change of fluorescence of a known amount of a suitable fluorophore in the reaction chamber. Under appropriate conditions the absorption spectrum of the chromophore overlaps with the emission spectrum of the fluorophore thereby allowing the change in fluorescence to be proportional to the intensity of color in the reaction and thus, proportional to the quantity of the substance of interest. Specifically, 8-methoxypyrene tri-sulfonic acid is used as the fluorophore.

16 Claims, No Drawings

MEASUREMENT OF COLOR REACTIONS BY MONITORING A CHANGE OF FLUORESCENCE

This is a continuation, of application Ser. No. 08/431, 194, filed on Apr. 27, 1995, which is a continuation of 08/174,613 filed on Dec. 28, 1993 which is a continuation of 08/016,654 filed Feb. 9, 1993, which in a continuation of 07/895,149 filed Jun. 5, 1992, which is a continuation of 07/238,710 filed Aug. 31, 1988, all now abandoned.

FIELD OF THE INVENTION

This invention relates to a process for determining the concentration of an unknown substance in a colorimetric reaction using a fluorometric reader.

BACKGROUND OF THE INVENTION

Chemical and enzymatic reactions are used to detect or quantitate the presence of certain substances in microbiological or other assays. Many of these tests rely on the development or change of color or fluorescence to indicate the presence or quantity of the substance of interest.

There are many examples of reactions used in Microbiology which rely on a color change. (*Bascomb, Enzyme Tests in Bacterial Identification,* 19 Meth. in Microbio. 105 (1987)). For example, a variety of organisms can be classified in large part by their pattern of fermentation, oxidation or assimilation of carbon sources. Fermentation of carbohydrates results in the production of acid which causes a decrease in pH. The drop in pH can be easily indicated by including a pH indicator like bromothymol blue or phenol red. With both indicators, acid conditions representing the fermentation of a particular carbohydrate result in a yellow color (changing from blue/green for bromothymol blue or pink/red for phenol red). The same approach can be adopted for a variety of carbohydrates, ranging from monosaccharides like glucose to polysaccnarides like inulin. In an analogous fashion, increasing pH can be followed. Assays for detecting the presence of decarboxylase and urease, and the ability to use malonate are based on an increase in pH, as indicated by a color change in the indicator.

Another approach to determine if an organism can degrade a particular substrate is to use a reagent which is capable of reacting with one or more of the intermediates or final products. For example, the detection of the reduction of nitrate to nitrite can be observed; if nitrite is formed, then a pink to deep red color will result when sulfanilic acid and alpha-napthylamine are added.

In contrast to the indirect detection of an enzymatic reaction illustrated by the nitrate/nitrite test, it is possible to use a synthetic analog of a natural substrate to directly indicate the presence of an enzyme. For example, methylene blue can be reduced under certain conditions by the action of reductase, resulting in a shift from blue to colorless.

Another test, the oxidase assay relies on the interaction of cytocnrome oxidase with N, N, N', N'-tetramethyl-p-phenylenedlamine producing a blue color.

Another example is the ability of microorganisms to degrade sulfur-containing amino acids as indicated by the production of $H_2S$. Typically, the organism is incubated with a high concentration of a sulfur-containing substrate (e.g. cysteine, cyscine) in an acid environment. The production of $H_2S$ is indicated by the formation of a black precipitate in the presence of ferric ammonium citrate.

Although the use of colorimetric reactions is widespread there are limitations, especially in the sensitivity of detection. In order to improve sensitivity or, in the case of identification of microorganisms, to decrease the time required to obtain a result, fluorescence-based methods frequently are used. Unfortunately, either it is not possibe to develop a fluorescent equivalent to every assay or the reagents themselves are highly toxic and difficult to commercialize.

Additionally, the general principle of fluorescence quenching has been accepted as a way to follow enzymatic or chemical reactions. For example, Fleminger et al. synthesized intcamolecularly quenched fluorogenic substrates for the assay of bacterial aminopeptidase (P. Fleminger et al., *Fluorogenic Substrates for Bacterial Aminopeptidase P and its Analogs Detected in Human Serum and Calf Lung,* 125 Eur. J. Biochem. 609 (1982). In this case, the fluorescence of the aminobenzoyl group is quenched by the presence of a nitrophenylalanyl group. When the enzyme is present, the nitrophenylalanyl group is cleaved, with a concomitant increase in the sample's fluorescence. A variety of enzymes have been assayed by this type of procedure, including hydrolytic enzymes, other amino- and carboxypeptidases and an endopeptidase (Yaron et al., *Intramolecularly Quenched Fluorogenic Substrates for Hydrolytic Enzymes,* 95 Anal. Biochem. 228 (1979));(Carmel et al., *Intramolecularly—Quenched Fluorescent Peptides as Fluorogenic Substrates of Leucine Aminopeptidase and Inhibitors of Clostridial Aminopeptidase,* 73 Eur. J. Biochem. 617 (1977));(Carmel et al., *An Intramolecularly Quenched Fluorescent Tripeptide as a Fluorogenic Substrate of Angiotensin-I-converting Enzyme and of Bacterial Dipeptidyl Carboxypeptidase,* 87 Eur. J. Biochem. 265 (1978); (Florentin et al., *A Highly Sensitive Fluorometric Assay for "Enkephalinase", a Neutral Metalloendopeptidase that Releases Tyrosine-Glycine-Glycine from Enkephalins,* 141 Anal. Biochem 62 (1984).

In each instance, a synthetic substrate containing a quenching group and a fluorescing group was generated in order to detect the activity of the enzyme. An alternative to this approach would involve the synthesis of a resonance energy transfer pair of fluorescing groups on a substrate molecule. In this application, cleavage by the enzyme of one of the groups would result in a decrease in fluorescence, since the critical distance would be exceeded, eliminating the transfer of energy. However, these approaches are limited to specifically designed substrates.

Presently, the monitoring of color end-product in chemical and microbial reactions is usually achieved in either of two ways; 1) The detection of color end-product can be achieved by visual observation and estimated semi-quantitatively, or 2) the detection of color end-products or loss of color can be achieved by measuring the intensity of color instrumentally. Spectrophotometers that measure light absorbance are commonly used for this purpose.

When measuring the concentration of any substance it is advantageous to use one instrument or one principle of measurement, otherwise cost is increased.

SUMMARY OF THE INVENTION

The present invention involves a process to detect/determine the concentration of an unknown substance in a colorimetric reaction using a fluorometric reader. More particularly, the change in color can be monitored by observing the change of fluorescence of a known amount of a suitable fluorophore. The principle is that under appropriate conditions the absorption spectrum of the chromophore overlaps the emission spectrum of the fluorophore thereby allowing the change in fluorescence to be proportional to the intensity of color in the reaction and consequently proportional to the quantity of the substance of interest.

Additionally, this invention relates to the use of an inert fluoropbore to monitor the extent of an enzymatic or chemical reaction based on the quenching of fluorescence by the formation of a colored product. There is no previous practice in the field with respect to the use of 8-methoxypyrene tri-sulfonic acid (hereinafter 8ME) as a fluorophore in monitoring color reactions. The advantages of 8ME over other fluorophores like esculin, 4-methylumbelliferone (hereinafter MEU) or aminomethylcoumarin (hereinafter AMC), are several. The 8ME molecule is quite soluble under a variety of conditions and is highly fluorescent. The most important characteristic (and advantage) of 8ME is the very slow degradation of the molecule, compared to other molecules which show a loss of fluorescence when stored in strongly acidic buffers.

DETAILED DESCRIPTION—BEST MODE

EXAMPLE I

In one embodiment the principle has been applied to: Detection of Indole. Indole forms a green-blue colored product when reacted with dimethylaminocinnamaldehyde (DMACA) at low pH. If a fluorophore like esculin at 0.5 mM or 8-methoxypyrene tri-sulfonic acid (8ME) at 0.3 mM is used, then the fluorescence will be quenched in the presence of indole and DMACA. The test is performed as follows:

PROCEDURE I

1. Make an inoculum in saline of a bacterial isolate equal to a 0.5 McFarland.

2. Add 100 microliters of the inoculum to a chamber containing dried material equivalent to 0.3% Tryptophan (Sigma), 0.1% Bacto-peptone (Difco), and 0.5 % $KPO_4$ (Sigma) at pH 7.6. A 100 microliter aliquot of the inoculum should be added to a control chamber made without Bacto-peptone or any other source of tryptophan.

3. Incubate for 2 to 5 hours at 35° C.

4. After the incubation, 50 microliters of DMACA with 0.5 mM esculin in 1.2M HCl is added and allowed to react for ten (10) minutes.

It indole is produced by the isolates, then the reaction mixture will turn green-blue. Measurement of fluorescence will show a marked decrease relative to the control, proportional to the indole present.

PROCEDURE II

Substitute 0.3 mM 8ME for esculin in Procedure I.

TABLE I

The following is representative of data collected with each of the procedures mentioned above.*

| Fluorescence Results | Reference Method | |
| --- | --- | --- |
| | Positive | Negative |
| Indole - Esculin | | |

TABLE I-continued

The following is representative of data collected with each of the procedures mentioned above.*

| Fluorescence Results | Reference Method | |
| --- | --- | --- |
| | Positive | Negative |
| Positive | 33 | 7 |
| Negative | 5 | 15 |
| Sensitivity = 87% | Specificity = 68% | |
| Indole - 8ME | | |
| Positive | 340 | 76 |
| Negative | 142 | 1688 |
| Sensitivity = 71% | Specificity = 96% | |

*The reference method for the indole test was performed as described in the package insert for the MicroScan GN ID only panel (Scientific Products). The incubation period is overnight.

EXAMPLE II

In a further embodiment the principle has been applied to: Beta-Lactamase. Beta-Lactamase is an enzyme which cleaves a bond in the lactam ring of penicillin. A carboxylic group is generated upon cleavage of the lactam ring. The cleavage destroys the potency of the antibiotic. One method to detect beta-lactamase activity is based on the competition between the open lactam ring and starch for $I_2$ molecules (iodometric). In the iodometric method, $I_2$ binds noncovalently to starch producing an intense blue-purple color. If a fluorophore like esculin or 8ME is present, then its fluorescence will be quenched. In the presence of beta-lactamase, the penicillin G is modified and the $I_2$ binds to the open lactam ring, resulting in a clearing of color from the chamber. As the chamber color clears fluorescence will increase. The test is performed as follows:

PROCEDURE I

1. Make an inoculum in saline of a bacterial isolate at 0.5 McFarland.

2. Add 100 microliters of the inoculum to a chamber containing dried material equivalent to 0.4 mg/ml penicillin G (Sigma), 0.02% starch (Difco) and 0.2 mM esculin.

3. Incubate for 2 to 5 hours at 35° C.

4. Following the incubation, 50 microliters of 2% Iodine solution (Scientific Products) is added, and incubated for at least ten (10) minutes.

If beta-lactamase is present, then the blue color will fade to clear and the fluorescence will increase.

PROCEDURE II

Substitute 0.0216 mM 8ME for the esculin in Procedure I.

TABLE II

The following is representative of data collected with each of the procedures mentioned above.*

| Fluorescence Results | Reference Method | |
| --- | --- | --- |
| | Positive | Negative |
| Beta-lactamase - Esculin | | |
| Positive | 11 | 4 |
| Negative | 2 | 16 |

TABLE II-continued

The following is representative of data collected with each of the procedures mentioned above.*

| Fluorescence Results | Reference Method | |
|---|---|---|
| | Positive | Negative |
| Sensitivity = 85% | Specificity = 80% | |
| Beta-lactamase - 8ME | | |
| Positive | 87 | 2 |
| Negative | 3 | 127 |
| Sensitivity = 97% | Specificity = 99% | |

*The reference method for the beta-lactamase test consists of using MicroScan POS conventional panels (Scientific Products) inoculated according to the package insert. The incubation period is overnight.

EXAMPLE III

In a further embodiment the principle has been applied to the detection of the enzyme oxidase. The presence or absence of this enzyme is used in identification of both fermentative and nonfermentative bacteria. The test detects the ability of organisms so oxidize the redox dye N, N, N', N'-tetramethyl-p-phenylenediamine (TMPD) in the presence of atmospheric oxygen by observation of a change in the reaction mixture from colorless to a blue. If a fluorophore like aminomethycoumarin (AMC) is included in the reaction mixture its fluorescence will be quenched. If the enzyme is present blue color appears in the chamber, the fluorescence of AMC will decrease proportionally.

PROCEDURE

1. Make an inoculum in saline of a bacterial isolate at 0.5 McFarland.
2. Add 50 microliters of the inoculum to a chamber containing dried material equivalent to 2.5 mM TMPD (Sigma), 0.5 mM N-acetycysteine, 4uM AMC, 50 mM succinic acid and 50 mM NaOH at pH 6.0. Add 50 microliters of saline to a control chamber containing the above ingredients.
3. Incubate for 2 to 5 hours at 35° C.
4. Measurement of the fluorescence will show a marked decrease relative to the control, and proportional to the oxidized TMPD. The reference method for the oxidase test consists of visual observation or the color change (colorless to blue) in the test chamber.

TABLE III

The following is representative of the data collected with the procedure mentioned above.

| Fluorescence Results | Reference Method | |
|---|---|---|
| | Positive | Negative |
| Positive | 11 | 0 |
| Negative | 0 | 121 |
| Sensitivity = 100% | Specificity = 100% | |

EXAMPLE IV

In a further embodiment the principle has been applied to the detection of the enzyme phenylalanine-ammonia-lyase (L-amino acid oxidase, phenylalanine test, PPA test). The presence of this enzyme has been used for specific recognition of the tribe Proteae and identification of *Moraxella phenylpyruvica*. The test detects the ability of the oranisms to deaminate an L-amino acid to form an alpha-keto acid + ammonia. Using the synthetic compound p-nitrophenylalanine as the substrate, if enzyme activity has occurred p-nitrophenylpyruvic acid is produced which can be detected, after addition of NaOH, by the appearance of a brownish color. If a fluorophore such as AMC at 25 uM is used, then its fluorescence will be quenched proportionally to the amount of p-phenyl pyruvic acid and NaOH. The test is performed as follows:

PROCEDURE

1. Make an inoculum in saline of a bacterial isolate at 0.5 McFarland.
2. Add 50 microliters of the inoculum to a chamber containing dried material equivalent to 5 mM DL-beta-(p-nitrophenol)alanine (Koch Light Laboratories), 0.1M Tris (hydroxy methyl) methylamine, 0.1M $KH_2PO_4$, and 25 microliters AMC at pH 8.0. Add 50 microliters of saline to a control chamber containing the above ingredients.
3. Incubate for 2 to 5 hours at 35° C.
4. After incubation add 25 microliters 0.2N NaOH to test and control chambers. If p-nitrophenylpyruvic acid is present the reaction mixture will turn yellow-brown. Measurement of fluorescence will show marked decrease relative to control and proportional to the p-nitrophenylpyruvic acid present.

TABLE IV

The following is representative of the data collected with the procedure mentioned above. The reference method for the phenylalanine-ammonia-lyase test consists of visual observation of the color change (colorless to brown) in the test chamber.

| Fluorescence Results | Reference Method | |
|---|---|---|
| | Positive | Negative |
| Positive | 13 | 1 |
| Negative | 1 | 110 |
| Sensitivity = 92.9% | Specificity = 99.1% | |

The use of an inert fluorophore to indicate changes in chromogenic assays requires 1) overlapping emission and absorption spectra and 2) the fluorophore fluoresces under the assay conditions. Hence a variety of fluorophore molecules could be used. For example, in some procedures any of the following compounds could be used:

8-methoxypyrene (8ME)

Esculin or derivatives

Acridine 6-methoxy-N-(-3-sulfopropyl) quinolinium inner salt

Quinine hydrochloride 8-hydroxypyrene-1,3,6 trisulfonic acid 1,3,6,8 pyrene tetrasulfonic acid Aminomethylcoumarin (AMC)

methylumbelliferone (MEU)

Beta-methylesculetin

8ME is preferred over each of these compounds at low pH. Under acid conditions, 8ME remains quite soluble and its fluorescence is not eliminated; moreover its fluorescence is retained even upon prolonged storage in acidic conditions.

It should be understood that the specification and examples are illustrative, but not limitative of the present invention and other embodiments with the spirit and scope of the invention will suggest themselves to those skilled in the art.

What is claimed is:

1. A method for detecting indole produced by a bacterial isolate based on the quenching of the fluorescence of 8-methoxypyrene tri-sulfonic acid or esculin, the method comprising:

inoculating a bacterial isolate into a chamber containing peptone and tryptophan;

incubating 2 to 5 hours;

adding at an acidic pH, dimethyl aminocinnamaldehyde containing 8-methoxypyrene tri-sulfonic acid or esculin, wherein said acidic pH is sufficiently low so that any indole would form a green-blue colored product when reacted with dimethyl aminocinnamaldihyde;

detecting with a fluorometric reader the extent of indole formation based on the quenching of fluorescence of the 8-methoxypyrene tri-sulfonic acid or esculin as a result of any green-blue product formed by the reaction of said indole and the dimethyl aminocinnamaldehyde.

2. A method for detecting beta-lactamase produced by a bacterial isolate based on a decrease in fluorescence quenching and an increase in fluorescence when compared to a control, the decrease in fluorescence quenching resultinq from the competitive binding of iodine to an open beta-lactamase ring, the method comprising:

inoculating a bacterial isolate into a chamber containing a growth supporting medium, starch, penicillin and esculin or 8-methoxypyrene tri-sulfonic acid;

incubating for 2 to 5 hours;

adding iodine solution; and detecting with a fluorometric reader the extent of beta-lactamase activity based on a decrease in fluorescence quenching and an increase in fluorescence when compared to a control, the decrease in fluorescence quenching resulting from the competitive binding of the iodine contained in said iodine solution to an open lactam ring of the penicillin instead of the starch present in the solution, the open lactam ring resulting from the cleavage of the lactam ring by the activity of beta-lactamase.

3. A method for detecting cytochrome oxidase produced by a bacterial isolate based on the quenching of the fluorescence of aminomethylcoumarin, the method comprising:

inoculating a bacterial isolate into a chamber containing succinic acid, N', N', N', N'-tetramethyl-p-phenylenediamine and aminomethylcoumarin;

incubating for 2 to 5 hours;

detecting with a fluorometric reader the extent of oxidase activity based on the quenching of fluorescence of the aminomethylcoumarin as a result of a blue product formed by the reaction of the oxidase with the N',N', N',N'-tetramethyl-p-phenylenediamine.

4. A method for detecting phenyl-alanine-ammonia-lyase produced by a bacterial isolate based on the quenching of the fluorescence of aminomethylcoumarin resulting from the production of p-nitrophenyl-pyruvic acid by enzymatic activity, the method comprising:

inoculating a bacterial isolate into a chamber containing potassium phosphate, p-nitrophenyl-alanine and aninonehylcoumarin;

incubating for 2 to 5 hours;

adding sodium hydroxide; and detecting with a fluorometric reader the extent of phenyl-alanine-ammonia-lyase formation based on the quenching of fluorescence of the aminomethylcoumarin, resulting from the production of p-nitrophenyl-pyruvic acid from the enzymatic activity, wherein the p-nitrophenyl-pyruvic acid reacts with the sodium hydroxide to form a brown colored product.

5. A method of using aminomethylcoumarin, 8-methoxypyrene tri-sulfonic acid or esculin as a fluorophore in monitoring color reaction for the detection of cytochrome oxidase produced by a bacterial isolate based on the quenching of fluorescence of said fluorophore, the method comprising:

inoculating a bacterial isolate into a chamber containing a medium, a substrate and a fluorophore selected from the group consisting of aminomethylcoumarin, 8-methoxypyrene tri-sulfonic acid and esculin;

incubating 2 to 5 hours;

monitoring the colored reaction produced by the cytochrome oxidase on the substrate; and detecting any cytochrome oxidase using a fluorometric reader based on the quenching of fluorescence of said fluorophore by said colored reaction when in the presence of cytochrome oxidase.

6. The method of claim 5 wherein the medium is succinic acid buffer and the substrate is N',N',N',N'-tetramethyl-p-phenylenediamine.

7. A method of using aminomethylcoumarin, 8-methoxypyrene tri-sulfonic acid or esculin as a fluorophore in monitoring color reaction for the detection of phenyl-alanine-ammonia-lyase or beta-lactamase produced by a bacterial isolate based on the quenching of fluorescence of said fluorophore, the method comprising:

inoculating a bacterial isolate into a chamber containing a medium, a substrate and a fluorophore selected from the group consisting of aminomethylcoumarin, 8-methoxypyrene tri-sulfonic acid and esculin;

incubating 2 to 5 hours;

adding a reagent to react with the product of the activity of phenyl-alanine-ammonia-lyase or beta-lactamase on their respective substrates to form a colored reaction;

monitoring the color reaction produced by the product of the activity of the phenyl-alanine-ammonia-lyase or beta-lactamase on their respective substrates on the reagent; and detecting any phenyl-alanine-ammonia-lyase or beta-lactamase using a fluorometric reader based on the change of quenching of fluorescence of said fluorophore by said colored reaction when in the presence of the product of the activity of phenyl-alanine-ammonia-lyase or beta-lactamase on their respective substrates.

8. The method of claim 7, where the fluorophore is aminomethylcoumarin, the medium is potassium phosphate buffer, the substrate is p-nitrophenylalanine and the reagent is sodium hydroxide.

9. The method of claim 7 where the fluorophore is 8-methoxypyrene tri-sulfonic acid or esculin, the medium is a growth supporting medium, the substrate is penicillin and the reagent is iodine.

10. A method of using 8-methoxypyrene tri-sulfonic acid or esculin as a fluorophore in monitorihg color reaction for the detection of indole produced by a bacterial isolate based on the quenching of fluorescence of said fluorophore, the method comprising:

inoculating a bacterial isolate into a chamber containing a medium, a substrate and a fluorophore selected from the group consisting of 8-methoxypyrene tri-sulfonic acid and esculin;

incubating 2 to 5 hours;

adding a reagent at an acidic pH to react with the indole to form a colored reaction wherein said acidic pH is sufficiently low so that any indole would form a colored product when reacted with said reagent;

monitoring the color reaction produced by the indole on the reagent; and detecting any indole using a fluorometric reader based on the quenching of fluorescence of said fluorophore by said colored reaction when in the presence of indole.

11. The method of claim 10 where the medium is a growth supporting medium of peptone, the substrate is tryptophan and the reagent is dimethylcinnamaldehyde.

12. A method of using aminomethylcoumarin, esculin or 8-methoxypyrene tri-sulfonic acid as a fluorophore in monitoring color reaction for the detection of phenyl-alanine-ammonia-lyase or beta lactamase produced by a bacterial isolate based on the quenching of fluorescence of said fluorophore, the method comprising:

inoculating a bacterial isolate into a chamber containing a medium and a substrate;

incubating 2 to 5 hours;

adding a reagent to react with the product of the activity of phenyl-alanine-ammonia-lyase or beta lactamase on their respective substrates to form a colored reaction, said reagent containing a fluorophore selected from the group consisting of aminomethylcoumarin, esculin, and 8-methoxypyrene tri-sulfonic acid;

monitoring the color reaction produced by the product of the activity of the phenyl-alanine-ammonia-lyase or beta lactamase on their respective substrates on the reagent; and detecting any phenyl-alanine-ammonia-lyase or beta-lactamase using a fluorometric reader based on the change of quenching of fluorescence of said fluorophore by said colored reaction when in the presence of the product of activity of phenyl-alanine-ammonia-lyase or beta-lactamase on their respective substrates.

13. The method of claim 12 where the fluorophore is aminomethylcoumarin, the medium is potassium phosphate buffer, the substrate is p-nitrophenylalanine and the reagent is sodium hydroxide.

14. The method of claim 12 where the fluorophore is esculin or 8-methoxypyrene tri-sulfonic acid, the medium is a growth supporting medium, the substrate is penicillin and the reagent is iodine.

15. A method of using 8-methoxypyrene tri-sulfonic acid or esculin as a fluorophore in monitoring color reaction for the detection of indole produced by a bacterial isolate based on the quenching of fluorescence of said fluorophore, the method comprising:

inoculating a bacterial isolate into a chamber containing a medium and a substrate;

incubating 2 to 5 hours;

adding a reagent at an acidic pH to react with the indole to form a colored reaction, said reagent containing a fluorophore selected from the group consisting of 8-methoxypyrene tri-sulfonic acid and esculin wherein said acidic pH is sufficiently low so that any indole would form a colored product when reacted with the reagent;

monitoring the color reaction produced by the indole on the reagent; and detecting any indole using a fluorometric reader based on the quenching of fluorescence of said fluorophore by said colored reaction when in the presence of indole.

16. The method of claim 15 where the medium is a growth supporting medium of peptone, the substrate is tryptophan and the reagent is dimethylcinnamaldehyde.

* * * * *

UNITED STATES PATENT AND TRADEMARK OFFICE
CERTIFICATE OF CORRECTION

PATENT NO. : 5,565,328
DATED : October 15, 1996
INVENTOR(S) : Shoshana Bascomb, et, al.

It is certified that error appears in the above-identified patent and that said Letters Patent is hereby corrected as shown below:

Column 1, Line 60: Delete "nylenedlamine" and insert –mylenediamine--.

Column 3, Line 8: Delete "fluoropbore" and insert –fluorophore--.

Column 5, Line 23: Delete "so" and insert –to--.

Signed and Sealed this

Twentieth Day of July, 1999

Attest:

Q. TODD DICKINSON

*Attesting Officer*     *Acting Commissioner of Patents and Trademarks*